United States Patent [19]

McPhee

[11] Patent Number: 5,800,405
[45] Date of Patent: Sep. 1, 1998

[54] SYRINGE ACTUATION DEVICE

[75] Inventor: Charles J. McPhee, Huntington Beach, Calif.

[73] Assignee: I-Flow Corporation, Lake Forest, Calif.

[21] Appl. No.: 794,211

[22] Filed: Jan. 30, 1997

Related U.S. Application Data

[63] Continuation-in-part of Ser. No. 969,874, Dec. 1, 1995, Pat. No. 5,599,315.

[51] Int. Cl.$^6$ .................................................. A61M 5/00
[52] U.S. Cl. ........................ 604/218; 604/135; 604/246
[58] Field of Search .................................. 604/218, 246, 604/156, 132–137, 187, 131

[56] References Cited

U.S. PATENT DOCUMENTS

| | | | |
|---|---|---|---|
| 2,472,116 | 6/1949 | Maynes | 128/218 |
| 2,565,081 | 8/1951 | Maynes | 128/218 |
| 2,591,457 | 4/1952 | Maynes | 128/218 |
| 3,880,163 | 4/1975 | Ritterskamp | 128/218 |
| 3,882,863 | 5/1975 | Sarnoff et al. | 128/218 |
| 4,316,463 | 2/1982 | Schmitz et al. | 128/218 |
| 4,381,006 | 4/1983 | Genese | 128/218 |
| 4,530,695 | 7/1985 | Phillips et al. | 604/184 |
| 4,597,754 | 7/1986 | Thill et al. | 604/154 |
| 4,623,330 | 11/1986 | Laby et al. | 604/63 |
| 4,755,172 | 7/1988 | Baldwin | 604/131 |
| 4,966,585 | 10/1990 | Gangemi | 604/131 |
| 4,997,420 | 3/1991 | LeFevre | 604/121 |
| 5,078,679 | 1/1992 | Reese | 604/51 |
| 5,100,389 | 3/1992 | Vaillancourt | 604/135 |
| 5,178,609 | 1/1993 | Ishikawa | 604/131 |
| 5,318,539 | 6/1994 | O'Neil | 604/118 |
| 5,320,609 | 6/1994 | Haber et al. | 604/135 |
| 5,330,430 | 7/1994 | Sullivan | 604/134 |
| 5,383,858 | 1/1995 | Eilly et al. | 604/152 |

FOREIGN PATENT DOCUMENTS

| | | |
|---|---|---|
| 0584569 | 5/1994 | European Pat. Off. . |
| 4222470 | 1/1993 | Germany . |

*Primary Examiner*—John D. Yasko
*Attorney, Agent, or Firm*—Klein & Szekeres, LLP

[57] ABSTRACT

A syringe actuation device includes a housing containing a spring-biased piston that applies an actuation force to a syringe plunger inserted into the housing. A pivoting mechanism causes the piston to pivot with respect to the longitudinal axis of the housing as the piston moves along that axis to actuate the plunger, whereby the axially-directed component of the force applied by the piston to the plunger remains substantially constant throughout the stroke of the piston. In one embodiment, the device comprises an internally-threaded outer sleeve having a longitudinal opening for receiving a pre-filled syringe with an extended plunger and a distal opening through which the syringe barrel extends, and an externally-threaded cylinder, containing the piston, that threads into the proximal end of the sleeve so as to bring the piston to bear against the plunger. The pivoting mechanism comprises a tapered internal diameter of the cylinder, and a sloped spring seat on the piston. In another embodiment, the device comprises a housing that contains a piston biased by a pair of springs, and a sleeve that receives a syringe barrel, with the plunger of the syringe extending from the proximal end of the sleeve. The proximal end of the sleeve is inserted into the housing through an opening in the distal end wall of the housing, so that the plunger seats against the piston. The pivoting mechanism comprises a narrowing internal housing width and springs of unequal spring constant and/or length.

51 Claims, 4 Drawing Sheets

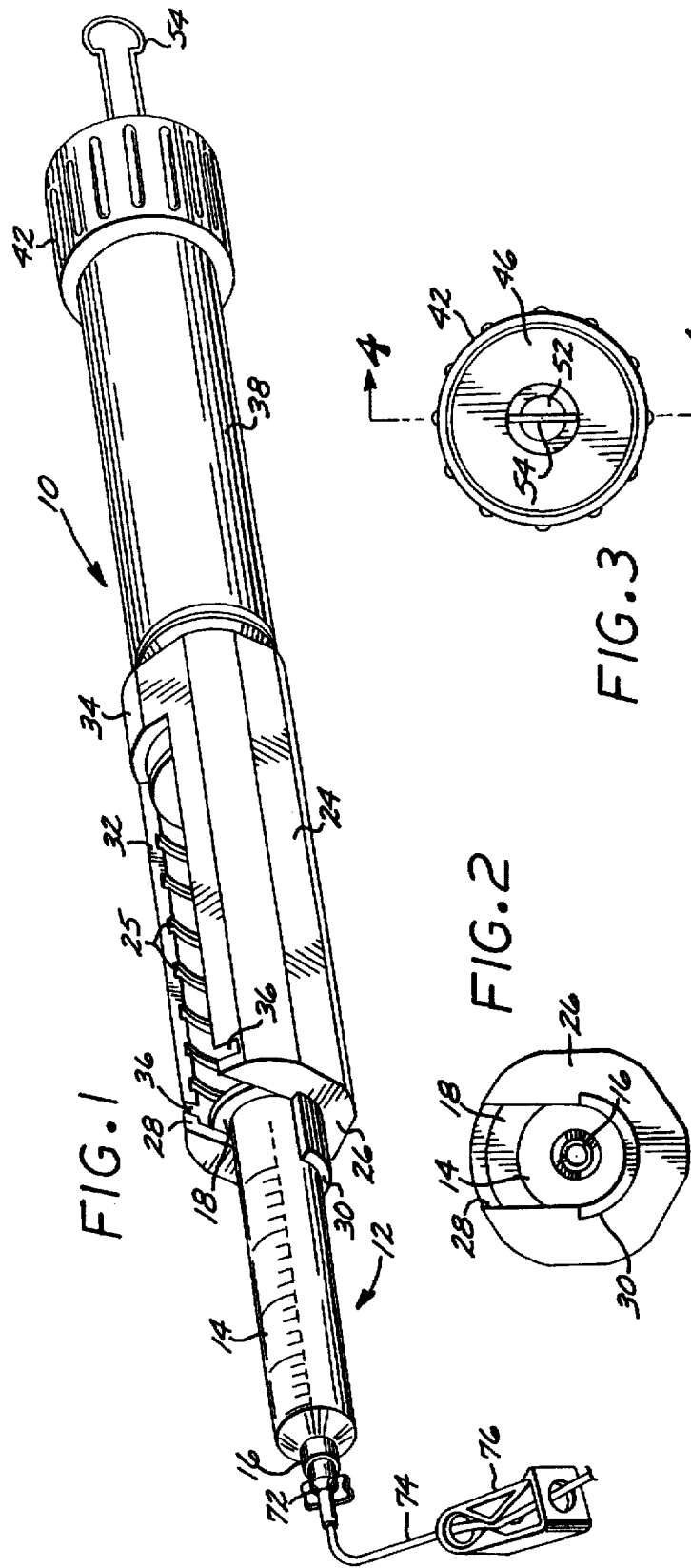

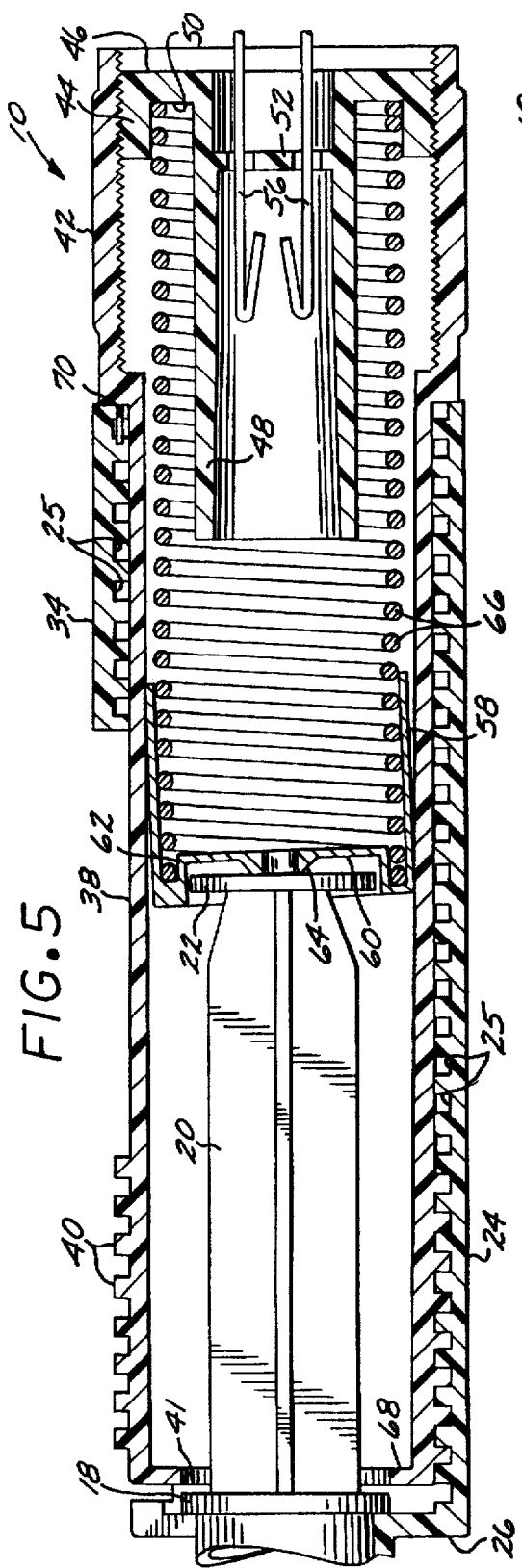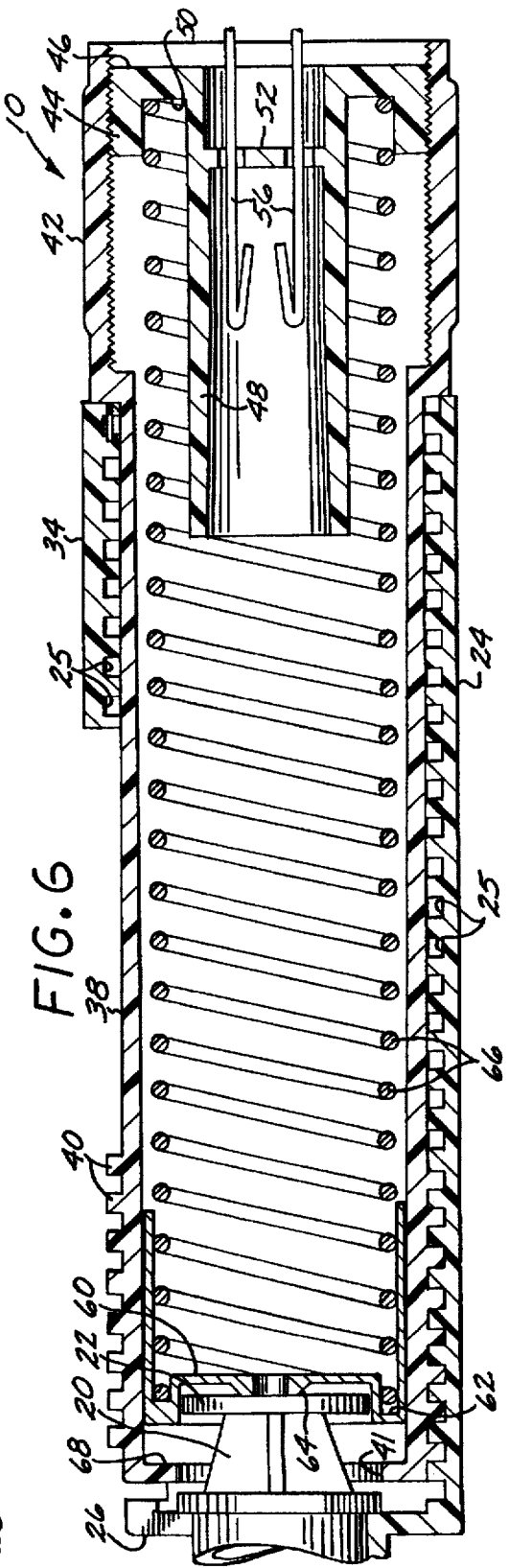

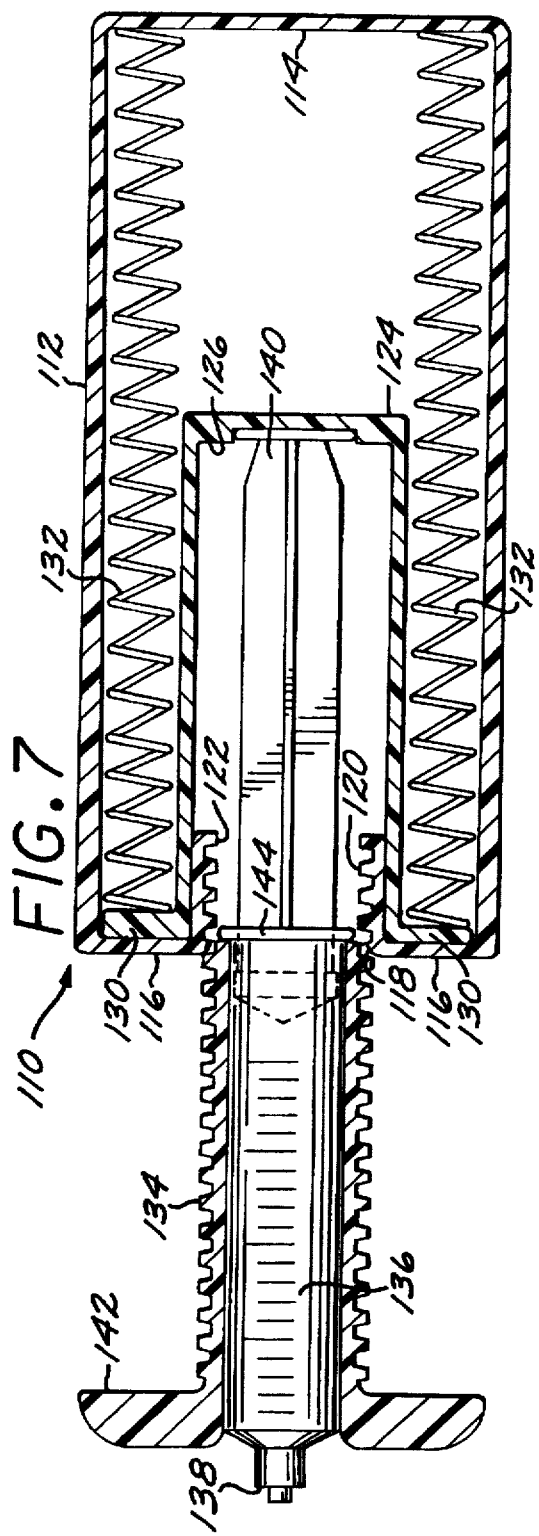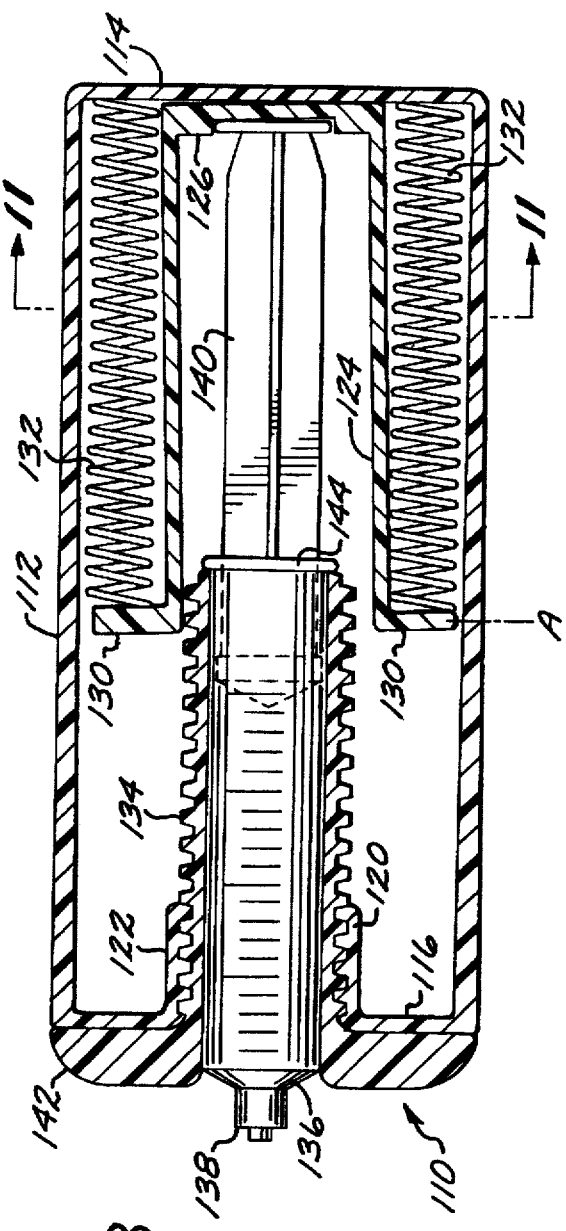

SYRINGE ACTUATION DEVICE

CROSS-REFERENCE TO RELATED APPLICATION

This application is a Continuation-in-Part of application Ser. No. 08/565,874, filed Dec. 1, 1995, now U.S. Pat. No. 5,599,315.

BACKGROUND OF THE INVENTION

This invention relates generally to the field of liquid infusion devices for medical applications. More specifically, it relates to mechanically-driven infusion devices used for the administration of a liquid medicament to a patient from a filled syringe into an intravenous (IV) administration system.

Various devices have been developed for the intravenous (IV) infusion of liquid medicaments into a patient at a controlled flow rate over an extended period of time. For example, gravity flow IV administration sets have been employed for many years, and more recently, IV administration sets with electrically powered pumps have been developed.

There are applications in which a more compact and inexpensive type of infusion device is desired or required. For example, in addition to direct infusion from a syringe, it is frequently necessary to infuse a secondary fluid into a primary IV flow from a gravity flow or electrically-pumped IV administration set. Also, infusion into an ambulatory patient frequently requires an infusion device that is less bulky, less complex, and easier to use than gravity flow or pump-powered devices. For such applications, relatively complex self-powered infusion devices are frequently used.

With a typical, manually actuated IV administration syringe, infusion over an extended period of time is usually impractical or inconvenient. Furthermore, even among syringes of the same size from the same manufacturer, the actuation forces required to provide a given fluid flow-versus-time profile vary greatly from syringe to syringe. Consequently, it is necessary to provide a sufficiently high actuation force to achieve a substantial degree of uniformity in fluid delivery from syringe to syringe. It has proven difficult consistently to achieve such sufficiently high syringe actuation forces with manually actuated syringes. To overcome these problems, the prior art has devised a variety of mechanisms for increasing the actuation force on the syringe throughout the infusion process. One type of syringe actuation mechanism is that which utilizes either internal or external springs to displace the plunger of the syringe. Examples of such mechanisms are shown in the following U.S. Pat. Nos.: 2,472,116—Maynes; 2,565,081—Maynes; 2,591,457—Maynes; 3,880,163—Ritterskamp; 3,882,863—Sarnoff et al.; 4,381,006—Genese; 4,530,695—Phillips et al.; 4,597,754—Thill et al.; 4,623,330—Laby et al.; 4,755,172—Baldwin; 4,966,585—Gangemi; 4,997,420—LeFevre; 5,078,679—Reese; 5,100,389—Vaillancourt; 5,178,609—Ishikawa; 5,318,539—O'Neil; 5,320,609—Haber et al.; 5,330,430—Sullivan; and 5,383,858—Reilly et al. Another example is shown in European Patent Application Publication No. 584 569A2.

The known prior art devices suffer from one or more shortcomings, however. For example, several of the above-listed patents show the use of "constant force" springs, which are elongated flat leaf springs coiled on a drum, to address this problem. Such springs, however, add expense, bulk, and mechanical complexity to the device.

Another drawback of some prior art devices is that they cannot be used with conventional syringes, and instead require the use of syringes that are specially-designed for use with the actuation device. Still another limitation of many prior art syringe actuation devices is that a relatively great physical effort is required to compress the plunger actuation spring, because these devices lack a sufficient mechanical advantage to reduce the "loading effort" any appreciable degree. Other syringe actuation devices of the prior art require the syringe to be disconnected from any downstream fluid conduits (such as an IV administration set) before being loaded into the actuation device. This limitation makes such devices disadvantageous for use in those clinical applications, such as IV administration procedures, in which it is advantageous to load a filled syringe into the syringe actuation device while the syringe is connected to the IV conduit.

It would therefore be a significant advancement over the prior art to provide a syringe actuation device that overcomes the aforementioned limitations. Specifically, it would be advantageous to provide such a device that yields improved uniformity in syringe-to-syringe fluid flow rates without a mechanism of undue complexity, and which is usable with conventional syringes of varying sizes. Furthermore, it would be advantageous to provide such a syringe actuation device that also may be loaded without undue physical effort, and that may receive a filled syringe while the syringe is connected to a downstream conduit.

SUMMARY OF THE INVENTION

Broadly, the present invention is a syringe actuation device for receiving and holding a filled conventional syringe having a plunger that is axially movable into the syringe barrel for expressing the contents therefrom, the device comprising a spring-biased piston that is engageable against the plunger to drive the plunger into the syringe barrel under the force of the spring.

More specifically, in accordance with a first preferred embodiment, the actuation device comprises an internally-threaded hollow outer sleeve with an open proximal end, and an externally-threaded hollow cylinder with a tapered internal diameter, that encloses a spring-biased piston, and that threads into the open distal end of the sleeve. The outer sleeve has a longitudinal opening parallel to its axis for receiving the fully-extended plunger of a pre-filled syringe, and a distal wall portion with an opening or slot through which the barrel of the syringe extends. The cylinder contains a coil spring extending axially within its hollow interior, the spring having a proximal end seated against a proximal end wall of the cylinder, and a distal end attached to the proximal side of the piston.

A significant point of novelty resides in the structure of the piston, and in its functional relationship with the tapered internal diameter of the cylinder. The piston is attached to the distal end of the spring so as to be pivotable from a canted orientation with respect to the cylinder's axis when the spring is compressed, to a coaxial orientation with respect to the cylinder's longitudinal axis when the spring is extended to a less compressed state. This pivoting function is facilitated by the tapered internal diameter of the cylinder, which decreases toward the distal end of the cylinder. This pivoting of the piston tends to equalize the axially-directed force component applied by the spring to the plunger as the spring decompresses, thereby substantially reducing the difference in flow rate from the syringe between the beginning and the end of the infusion process.

In use, the cylinder is backed out of the outer sleeve to its most proximal axial position, thereby allowing a pre-filled syringe to be installed in the outer sleeve through the longitudinal opening. The plunger of the pre-filled syringe is extended in the proximal direction to its withdrawn position, and the outlet tip of the syringe is connected to a fluid conduit (e.g., an IV line). Flow from the syringe is occluded by means of a line clamp or an in-line valve or the like. As the cylinder is threaded into the outer sleeve, the distal side of the piston bears against the thumb rest at the proximal end of the plunger. Because fluid flow out of the syringe is blocked, the plunger cannot be displaced axially into syringe barrel. Consequently, the continued threading of the cylinder into the outer sleeve causes the plunger to bear against the piston so as to displace the piston axially in the proximal direction, against the force of the spring, thereby compressing the spring.

When the conduit to which the syringe is connected is opened to permit fluid flow, the spring is permitted to decompress. The force of the spring as it decompresses pushes the piston axially in the distal direction against the plunger, thereby pushing the plunger axially into the barrel of the syringe to express the contents of the barrel out of the outlet tip of the syringe.

When the spring is at its fully compressed position, the total force it can apply to the plunger is substantially greater than the force applied to the plunger near the end of the distally-directed stroke of the piston. (Typically, for example, the spring force may decrease by twenty per cent or more from the beginning to the end of the distal stroke of the piston.) To compensate, at least in part, for this decrease in force, the piston is canted with respect to the axis of the cylinder when the spring is in its compressed state. This canting is facilitated by the internal diameter of the cylinder being measurably greater than the external diameter of the piston at the point along the length of the cylinder where the piston resides at the beginning of its distal stroke. Because of this canting of the piston, at the beginning of the piston's distally-directed stroke, when the total spring force is at its greatest, a part of the spring force is directed radially, rather than axially. Therefore, something less than the total spring force is applied to push the plunger into the syringe barrel.

As the piston is displaced distally by the decompression of the spring, the piston pivots gradually toward an orientation in which its plane is orthogonal to the axis of the cylinder, guided by the gradual reduction in the internal diameter of the cylinder. Thus, as the total spring force decreases as the spring decompresses, a larger proportion of the total spring force is directed axially against the plunger. Accordingly, the magnitude of the axially-directed component of the spring force remains nearly constant throughout a substantial portion of the distally-directed stroke of the piston, thereby resulting in a nearly constant fluid flow from the syringe throughout a substantial portion of the axial travel of the plunger.

In accordance with a second preferred embodiment, the actuation device comprises a housing with a closed proximal end wall and a distal end wall having an opening centrally located therein. The internal width of the housing narrows slightly from its proximal end to its distal end. An internally-threaded retention element extends proximally from the distal end wall opening. Contained within the housing is a piston having a closed proximal end and an open distal end sized to slide over the exterior surface of the retention element. A pair of outwardly-extending flanges extend from opposite sides of the distal end of the piston. Each of the flanges serves as a distal spring seat for the distal end of one of a pair of elongate coil springs, the proximal ends of which seat against the proximal housing end wall. The piston is disposed for longitudinal reciprocation within the housing between a distal position, in which the springs are decompressed and the flanges seat against the distal housing end wall on diametrically opposite sides of the distal end wall opening, and a proximal position, in which the springs are compressed, and the proximal end of the piston seats against the proximal housing end wall.

The device further comprises an open-ended, externally-threaded sleeve that has an interior passage dimensioned to receive the barrel of a conventional infusion syringe, with the outlet tip of the syringe extending from the distal end of the sleeve, and the plunger of the syringe extending from the proximal end of the sleeve. The external threads of the sleeve mate with the internal threads of the retention element in the housing, so that the sleeve can be threaded into and out of the retention element and the distal end wall opening of the housing. The distal end of the sleeve is configured as a handle to facilitate this threading action.

In use, a filled syringe, with its plunger partially or fully extended or withdrawn from the barrel, and with flow from its outlet tip blocked, is inserted into the proximal end of the sleeve until the outlet tip of the syringe emerges from the distal end of the sleeve. The plunger, which extends through the proximal end of the sleeve, is inserted through the distal end wall opening of the housing and into the interior of the piston, seated against the proximal end of the piston. At this point, the sleeve is positioned to be threaded into the retention element, with the proximal end of the sleeve adjacent the distal end wall opening.

As the sleeve is threaded into the opening and the retention element, the plunger pushes against the proximal end of the piston, thereby pushing the piston proximally against the force of the springs, which are thereby compressed. When flow from the outlet tip is permitted, the springs decompress, pushing the plunger distally to discharge the contents of the syringe.

As in the first embodiment, a significant point of novelty of the second embodiment lies in the ability of the piston to pivot with respect to the longitudinal axis of the housing as it travels from its proximal position to its distal position. Specifically, one of the two springs has a slightly larger spring constant than the other. Thus, when the springs are compressed with the piston in its proximal position, the piston is canted with respect to the longitudinal axis of the housing due to the imbalance in the forces applied by the springs to the two flanges of the piston. As the piston travels distally, the magnitudes of the forces applied by the two springs to their respective flanges converge as the springs decompress, so that the piston gradually pivots to a coaxial orientation with respect to the longitudinal axis of the housing. This pivoting action is facilitated by the narrowing internal width of the housing, which is measurably greater than the external width across the flanges of the piston at the point along the length of the housing at which the flanges reside when the piston is at its proximal position, and approximately equal to (or very slightly greater than) the external width across the piston flanges near the distal end of the housing. As in the first embodiment, the pivoting of the piston tends to maintain the magnitude of the axially-directed component of the spring force nearly constant through a substantial portion of the distally-directed stroke of the piston, thereby resulting in a nearly constant flow rate from the syringe throughout a substantial portion of the axial travel of the plunger.

From the foregoing, it can be seen that a syringe actuation device in accordance with the present invention provides sufficient syringe actuation force substantially to overcome non-uniformity in syringe-to-syringe operational characteristics, with a more nearly constant fluid flow rate as the syringe is emptied without the use of "constant force" springs and their attendant complexities. Furthermore, conventional syringes of various sizes can be used with the present invention, and these syringes can be installed in the actuation device of the present invention while they are connected to a fluid flow line. These and other advantages of the present invention will be more fully appreciated from the detailed description that follows.

BRIEF DESCRIPTION OF THE DRAWINGS

FIG. 1 is a perspective view of a syringe actuation device in accordance with a preferred embodiment of the present invention, showing the device with a filled syringe installed therein, and showing the syringe connected to an IV line or the like;

FIG. 2 is an elevational view of the distal end of the syringe actuation device of FIG. 1, with a filled syringe installed therein;

FIG. 3 is an elevational view of the proximal end of the syringe actuation device of FIG. 1;

FIG. 4 is a cross-sectional view taken along line 4—4 of FIG. 3, showing the syringe actuation device before the cylinder is threaded into the outer sleeve;

FIG. 5 is a cross-sectional view similar to that of FIG. 4, showing the spring of the syringe actuation device compressed by the syringe plunger after the cylinder has been threaded into the outer sleeve;

FIG. 6 is a cross-sectional view similar to that of FIG. 5, showing the syringe plunger axially displaced in the distal direction by the decompression of the spring;

FIG. 7 is a cross-sectional view of a syringe actuation device in accordance with a second preferred embodiment of the invention, showing the device with a pre-filled syringe partially installed therein;

FIG. 8 is a cross-sectional view, similar to that of FIG. 7, showing the pre-filled syringe fully installed in the syringe actuation device of FIG. 7, ready for use;

DETAILED DESCRIPTION OF THE PREFERRED EMBODIMENTS

Figure 9:
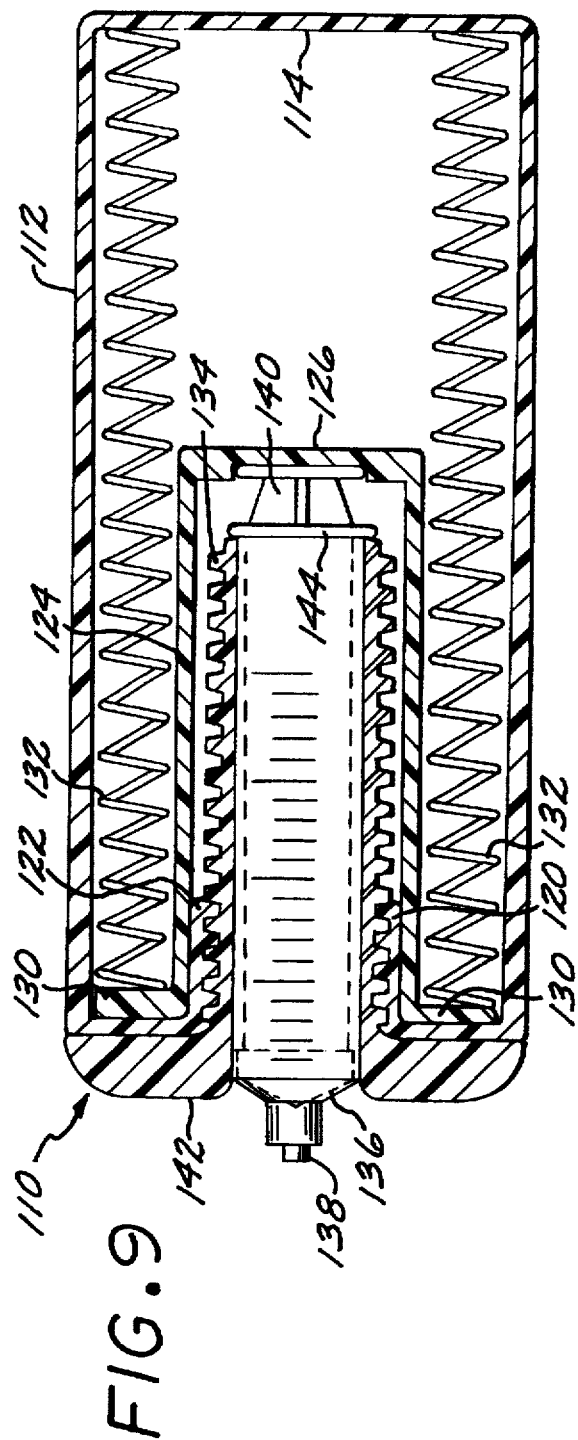
FIG. 9 is a cross-sectional view, similar to that of FIG. 8, showing the syringe after its contents have been discharged using the syringe actuation device of FIG. 7.
Figure 11:
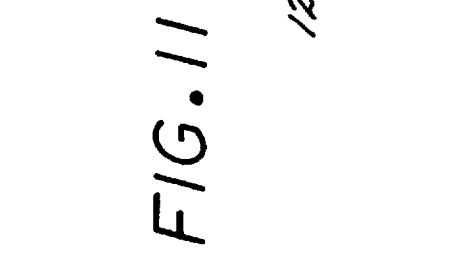
FIG. 11 is a cross-sectional view taken along line 11—11 of FIG. 8.
Figure 10:
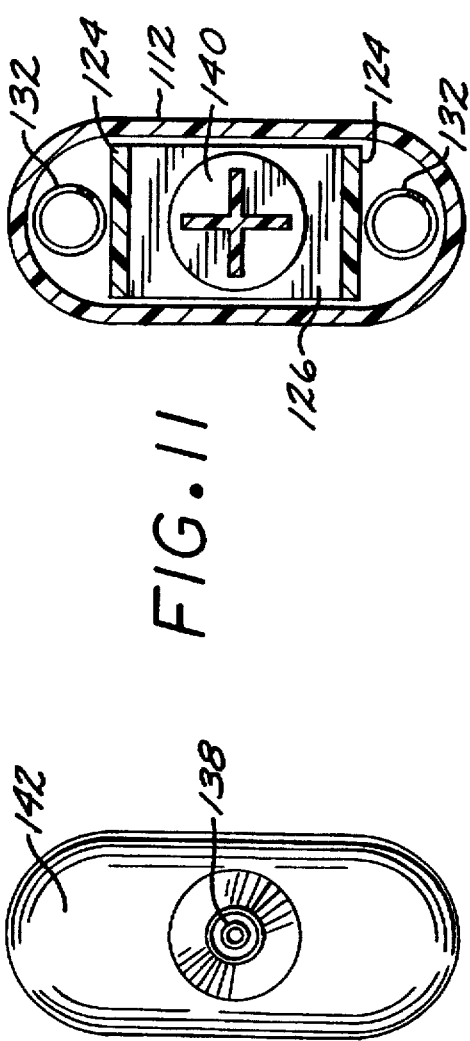
FIG. 10 is an elevational view taken from the left side of FIG. 9, showing the distal end of the syringe actuation device of FIG. 7 with the syringe installed therein.

Referring first to FIGS. 1–6, a syringe actuation device 10, in accordance with a first preferred embodiment of the invention, is shown with a conventional infusion syringe 12 installed therein for action.

The syringe 12 is of conventional design, comprising a hollow cylindrical chamber or barrel 14 communicating with an outlet tip 16 at its distal end. The proximal end of the barrel 14 terminates in an annular flange 18. A plunger 20 is disposed for axial movement within the barrel 14 between a proximal withdrawn position and a distal inserted position. The proximal end of the plunger 20 terminates in a flattened plate or thumb rest 22.

The actuation device 10 comprises a hollow outer sleeve 24 that has an internal thread 25 throughout its length. The sleeve 24 has an open proximal end and a distal end wall 26 interrupted by a vertical slot 28 that is dimensioned to receive the syringe barrel 14. Extending distally from the distal end wall 26 below the slot 28 is a semi-cylindrical support 30 upon which the syringe barrel 14 rests as it extends distally from the end wall 26. Extending proximally from the slot 28 is a longitudinal opening 32, parallel to the axis of the sleeve 24, that extends proximally along a substantial portion of the length of the sleeve 24, terminating at an annular collar portion 34 adjacent the proximal end of the sleeve 24. The width of the longitudinal opening 32 is greater than the width of the plunger 20, so that the plunger 20 may be installed in the sleeve 24 through the axial opening 32. A pair of arcuate slots 36 extend a short distance circumferentially from opposite sides of the longitudinal opening 32 near the distal end thereof. The arcuate slots 36 provide clearance for accommodating the flange 18 at the proximal end of the syringe barrel 14.

A hollow cylinder 38 has a distal portion with an external thread 40 that mates with the internal thread 25 of the sleeve 24, so that the distal end of the cylinder 38 can be threaded into the sleeve 24 through the open proximal end of the latter. The distal end of the cylinder 38 has a central aperture 41 dimensioned to allow the passage therethrough of the syringe plunger 20, as will be explained below. The internal diameter of the cylinder 38 decreases gradually from its proximal end to its distal end, for reasons that will be explained below.

The cylinder 38 may advantageously be provided with an increased-diameter gripping portion 42 adjacent its proximal end. The interior of the gripping portion 42 may advantageously be internally threaded to mate with an externally-threaded peripheral collar 44 of a closure member 46 that closes the proximal end of the second sleeve 38. The closure member 46 includes a hollow tubular sheath portion 48 that extends distally into the interior of the cylinder 38. Between the collar 44 and the sheath portion 48, the interior surface of the closure member 46 defines an annular surface that functions as a fixed spring seat 50, as will be described below. The interior of the sheath portion is closed near its proximal end by an end wall 52. A retractable wire hanger 54 has a pair of distally-extending legs 56 that pass through a pair of diametrically-opposed apertures in the end wall 52 and into the interior of the sheath portion 48. The hanger 54 may thus be selectively withdrawn from the sheath portion 48 when it is needed, and pushed into the sheath portion 48 when it is not needed.

An axially-movable piston 58 is disposed within the cylinder 38 adjacent the distal end thereof. The piston 58 comprises a hollow cylindrical member with an external diameter that is slightly less than the minimum internal diameter of the cylinder 38. The proximal end of the piston 58 is open, and the distal end of the piston 58 is closed by a circular pressure plate 60, the proximal surface of which is formed with a peripheral annular groove 62. The groove 62 has a maximum depth at one circumferential position, and it progressively decreases in depth toward the diametrically opposite circumferential position. The groove 62, with its varying depth, provides a movable spring seat that tends to equalize the force applied to the piston throughout its travel, as will be explained below. The distal surface of the pressure plate 60 is recessed to form a seat for the thumb rest 22 of the syringe plunger 20. A central protuberance 64, the purpose of which will be explained below, extends distally from the center of the pressure plate distal surface.

Disposed longitudinally in the cylinder 38 so as to be concentric with the sheath portion 48 is a coil spring 66 having a proximal end that seats against the fixed spring seat 50 defined by the closure member 46, and a distal end that seats in the groove 62 in the pressure plate 60 of the piston 58. The spring 66 has a compressed position (FIG. 5) and an extended position (FIG. 6), but it is under some compression even in its extended position. The spring 66, being substantially coaxial with the cylinder 38, thus applies an axially-directed force to the piston 58 so as to urge the piston 58 distally, the distal travel of the piston 58 being limited by an annular lip 68 directed radially inwardly around the central aperture 41 at the distal end of the cylinder 38.

The outer sleeve 24 and the cylinder 38 may advantageously be pre-assembled, so that the latter is pre-threaded part of the way into the former. With such an arrangement, it may be desired to make these two components inseparable, whereby the cylinder 38 is incapable of being backed all the way out of the sleeve 24. To this end, the most proximal turn of the internal thread 25 of the sleeve 24 may be obstructed with a longitudinally-disposed pin 70 or equivalent obstructing element.

The operation of the actuation device 10 may now be readily understood. The outlet tip 16 of a prefilled syringe 12 is connected, by a conventional connector fitting 72, to a flexible conduit 74, such as an IV line. Once the syringe 12 is filled, outflow of liquid from it is blocked by a clamp 76, of conventional design, applied to the conduit 74 downstream from the outlet tip 16. With the barrel 14 of the syringe 12 filled, the plunger 20 is extended to its proximal withdrawn position, and, since flow from the syringe 12 is occluded, the plunger 20 cannot be moved to its distal inserted position.

With the cylinder 38 of the actuation device 10 at its most proximal position with respect to the sleeve 24, i.e., threaded into the outer sleeve 24 only about as far as the collar portion 34 of the latter, the longitudinal opening 32 of the sleeve 24 provides access for the plunger 20 of the syringe 12 to be received within the interior of the sleeve 24, with the syringe barrel 14 being received in the vertical slot 28 in the distal end wall 26 of the sleeve 24, as best shown in FIG. 1. When the syringe 12 is so situated, the flange 18 at the proximal end of the syringe barrel 14 is cleared through the arcuate slots 36 near the distal end of the longitudinal opening 32, so that the flange 18 seats against the interior (proximal) surface of the distal end wall 26, as shown in FIGS. 4 through 6.

The initial proximal position of the cylinder 38 with respect to the syringe 12 installed within the sleeve 24 is shown in FIG. 4. The spring 66 is in its most decompressed or extended position, whereby the piston 58 is urged to its most distal position in abutment against the lip 68 at the distal end of the cylinder 38. There is, as yet, no contact between the pressure plate 60 of the piston 58 and the thumb rest 22 of the plunger 20.

As the cylinder 38 is threaded distally into the sleeve 24, the protuberance 64 of the piston pressure plate 60 begins to bear against the plunger thumb rest 22. Since the plunger 20 is restrained from movement in the distal direction, as described above, and since the syringe 12 as a whole is restrained from movement in the distal direction by the abutment of the barrel flange 18 against the distal end wall 26 of the sleeve 24, the engagement of the pressure plate protuberance 64 against the thumb rest 22 causes the spring 66 to be compressed. Maximum compression is reached when the cylinder 38 is threaded into the sleeve 24 to its most distal position, i.e., when the gripping portion 42 of the cylinder 38 abuts against the collar portion 34 of the sleeve 34, as shown in FIG. 5. When the spring 66 is thus compressed, the piston 58 is canted or tilted with respect to the longitudinal axis of the cylinder 38, as shown in FIG. 5, as a result of the varying depth of the spring-seating groove 62 in the pressure plate and the tapered internal diameter of the cylinder 38, as mentioned above. Because the protuberance 64 has a relatively small surface area bearing against the thumb rest 22, frictional forces between the piston 58 and the thumb rest 22 are substantially reduced, thereby providing easier threading of the cylinder 38 into the sleeve 24, and reducing the rotational torque applied to the plunger 20 by the threading process.

When infusion is to begin, the clamp 76 is released, thereby allowing the outflow of the fluid contents of the syringe barrel 14 through the outlet tip 16 and the conduit 74. With fluid flow now unblocked, the plunger 20 may now be moved distally into the barrel 14 to express the fluid contents therefrom. Such movement of the plunger 20 is effected by the decompression of the spring 66, the force of which urges the piston 58 distally against the thumb rest 22 of the plunger 20, thereby forcing the plunger 20 to move distally into the syringe barrel 14 to express the contents of the syringe 12 out of the outlet tip 16.

As the piston 58 is moved distally by the spring 66, the engagement between the piston 58 and the tapered internal wall surface of the cylinder 38 causes the piston 58 to pivot so as to reduce the amount of its canting with respect to the longitudinal axis of the cylinder 38. In other words, as the piston 58 is displaced distally by the decompression of the spring 66, the piston 58 pivots gradually toward an orientation in which its axis is substantially coaxial with the longitudinal axis of the cylinder 38, as shown in FIG. 6. This pivoting action is facilitated by the protuberance 64 on the distal surface of the pressure plate 60.

The purpose of the pivoting action of the piston 58 is as follows: When the spring 66 is in its compressed the state (FIG. 5), the axis of the piston 58 is canted with respect to the axis of the cylinder 38. Thus, at the beginning of the piston's distally-directed stroke, when the total spring force is at its greatest, a part of the spring force is directed radially, rather than axially. Therefore, something less than the total spring force is applied to push the plunger 20 into the syringe barrel 14. As the piston 58 is displaced distally by the decompression of the spring 66, the piston 58 pivots gradually toward the orientation in which its axis is substantially coaxial with the axis of the cylinder 38. Thus, as the total spring force decreases as the spring 66 decompresses, a larger proportion of the total spring force is directed axially against the plunger 20. Accordingly, the magnitude of the axially-directed component of the spring force remains nearly constant throughout a substantial portion of the distally-directed stroke of the piston 58, thereby resulting in a nearly constant fluid flow rate from the syringe 12 throughout a substantial portion of the axial travel of the plunger 20.

When the syringe 12 is empty, the cylinder 38 is backed out of the sleeve 24 a short distance to separate the piston pressure plate 60 from the thumb rest 22, so that the syringe can simply be removed from the actuation device 10.

FIGS. 7 through 11 illustrate a second preferred embodiment of the invention. In accordance with this second embodiment, a syringe actuation device 110 comprises a housing 112 with a closed proximal end wall 114 and a distal end wall 116 having a distal end opening 118 centrally located therein. The internal width of the housing 112 narrows slightly from its proximal end to its distal end. A retention element, comprising a pair of diametrically-opposed, internally-threaded, arcuate members 120, 122, extends proximally from the distal end opening 118. Contained within the housing 112 is a piston 124 having a proximal end wall 126 and an open distal end. The piston 124 is internally dimensioned and configured to slide over the exterior surfaces of the arcuate members 120, 122. Extending from opposite sides of the distal end of the piston 124 is a pair of outwardly extending flanges 130, each of which serves as a distal spring seat for the distal end of one of a pair of elongate coil springs 132, the proximal ends of which seat against the proximal housing end wall 114. The piston 124 is disposed for longitudinal reciprocation within the housing 112 between a distal position (FIGS. 7 and 9), in which the springs 132 are decompressed and the flanges 130 seat against the distal housing end wall 116 on diametrically opposite sides of the distal end opening 118, and a proximal position (FIG. 8), in which the springs 132 are compressed, and the proximal end wall 126 of the piston 124 seats against the proximal housing end wall 114.

The device 110 further comprises an open-ended, externally-threaded sleeve 134 that has an interior passage dimensioned to receive the barrel of a conventional infusion syringe 136, with the outlet tip 138 of the syringe 136 extending from the distal end of the sleeve 134, and the plunger 140 of the syringe 136 extending from the proximal end of the sleeve 134. The external threads of the sleeve 134 mate with the internal threads of the arcuate members 120, 122 of the retention element, so that the sleeve 134 can be threaded into and out of the retention element and the distal end opening 118 of the housing 112. The distal end of the sleeve 134 is configured as a handle 142 to facilitate this threading action.

In use, a filled syringe 136, with its plunger 140 fully extended, and with flow from its outlet tip 138 blocked (as described above) is inserted into the proximal end of the sleeve 134 until the outlet tip 138 of the syringe 136 emerges from the distal end of the sleeve 134. As is typical with syringes of the kind used in the present invention, the proximal end of the syringe barrel terminates in a flange 144 that abuts against the proximal end of the sleeve 134. The plunger 140, which extends through the proximal end of the sleeve 134, is inserted through the distal end opening 118 of the housing 112 and into the interior of the piston 124, seated against the proximal 126 end wall of the piston 124. At this point, as shown in FIG. 7, the sleeve 134 is positioned to be threaded into the retention element, with the proximal end of the sleeve 134 adjacent the distal end opening 118.

As the sleeve 134 is threaded into the distal end opening 118 and the retention element, the plunger 140 pushes against the proximal end 126 of the piston 124, thereby pushing the piston 124 proximally against the force of the springs 132, which are thereby compressed. This threading is continued until the piston 124 is pushed to its proximal position, as shown in FIG. 8, with the springs 132 fully compressed. When flow from the outlet tip 138 is permitted, the springs 132 decompress, pushing the piston 124 toward its distal position. With the proximal end wall 126 of the piston 124 bearing against the plunger 140, the plunger 140 is pushed distally, to its inserted position, to discharge the contents of the syringe 136. The threaded engagement between the sleeve 134 and the arcuate members 120, 122 of the retention element locks the sleeve 134 in place, thereby preventing the sleeve 134 from being displaced relative to the retention element by the force applied to the plunger 140 by the piston 124. The distal travel of the piston 124 is halted by the abutment of the flanges 130 against the distal end wall 116, at which point the piston 124 is at its distal position, as shown in FIG. 9.

When the syringe 136 has been emptied, the sleeve 134 is threaded out of the retention element and the distal end opening 118, and the empty syringe 136 is then removed from the sleeve 134. The sleeve 134 is then ready to receive another syringe for installation in the housing 112 as described above.

As in the first embodiment, a significant point of novelty of the second embodiment lies in the ability of the piston 124 to pivot with respect to the longitudinal axis of the housing 112 as it travels from its proximal position to its distal position. Specifically, one of the two springs 132 has a slightly larger spring constant than the other. Thus, when the springs 132 are compressed with the piston 124 in its proximal position (FIG. 8), the piston 124 is canted with respect to the longitudinal axis of the housing 112 due to the imbalance in the forces applied by the springs 132 to the two flanges 130 of the piston 124. In this position, the total force applied to the plunger 140 by the piston 124 is at its maximum magnitude, but the axially-directed plunger actuation component of the force is less than the total applied force. As the piston 124 travels distally, the magnitudes of the forces applied by the two springs 132 to their respective flanges 130 converge as the springs 132 decompress, so that the piston 124 gradually pivots to a coaxial orientation with respect to the longitudinal axis of the housing 112, as shown in FIG. 9. When the piston 124 is in its distal position (FIG. 9), the magnitude of the total force applied by the piston 124 to the plunger 140 is less than its maximum value, while the axially-directed actuation component of that force is approximately equal to the total force.

The above-described pivoting action is facilitated by the narrowing internal width of the housing 112, which is measurably greater than the external width across the flanges 130 of the piston 124 at a point "A" (FIG. 8) along the length of the housing 112 at which the flanges 130 reside when the piston 124 is at its proximal position, and approximately equal to (or very slightly greater than) the external width across the piston flanges 130 near the distal end of the housing 112. As in the first embodiment, the pivoting of the piston 124 tends to maintain the magnitude of the axially-directed component of the spring force nearly constant through a substantial portion of the distally-directed stroke of the piston 124, thereby resulting in a nearly constant flow rate from the syringe 136 throughout a substantial portion of the axial travel of the plunger 140.

The pivoting action can also be imparted by using springs of unequal length. Unequal length springs can be accommodated, for example, by making one of the flanges 130 thicker than the other, or by sloping the proximal housing end wall 114.

It will be appreciated from the foregoing description that the actuation device in accordance with the present invention can be employed with conventional syringes of a variety of sizes, yielding nearly constant fluid flow from such syringes throughout a substantial portion of the distal stroke of the plunger. Moreover, sufficient force is generated for satisfactory actuation of even relatively large capacity syringes, i.e., up to about 60 cc or more, with a high degree of uniformity in fluid flow characteristics among syringes of equal sizes and similar types. Furthermore, the syringe can readily be installed in the device even while the syringe is connected to an IV line or the like. Finally, these advantages are achieved with a mechanism that is relatively simple and inexpensive to manufacture and easy to operate.

While two preferred embodiments of the invention have been described herein, it will be appreciated that a number of variations and modifications will suggest themselves to those skilled in the pertinent arts. Such variations and modifications may be considered within the spirit and scope of the present invention, as defined in the claims that follow.

What is claimed is:

1. A device for applying an axially-directed actuation force to a syringe plunger, of the type including a force-applying mechanism engageable with the plunger to apply the actuation force thereto, characterized by the force applying mechanism having a first position at which the magnitude of the total force applied to the plunger is at a maximum value but the axially-directed actuation force is less than the total force applied to the plunger, and a second position at which the magnitude of the total force applied to the plunger is less than its maximum value and the axially-directed force is approximately equal to the total force applied to the plunger, wherein the force-applying mechanism comprises:

a housing having a proximal end and a distal end with an opening dimensioned to receive the plunger;

a piston disposed for longitudinal movement within the housing between a proximal position and a distal position, the piston being seatable against the plunger when the plunger is received in the housing through the opening in the distal end;

first and second springs disposed between the piston and the proximal end of the housing so as to bias the piston toward its distal position; and pivoting means, operative on the piston, for canting the piston with respect to the longitudinal axis of the housing when the piston is in its proximal position, and for causing the piston to pivot as it moves toward its distal position until the piston is oriented substantially coaxially with the longitudinal axis when the piston is at its distal position.

2. The device of claim 1, wherein the pivoting means comprises an internal width of the housing that narrows from the proximal end to the distal end.

3. The device of claim 2, wherein the pivoting means further comprises the first spring having a larger spring constant than the second spring.

4. The device of claim 2, wherein the pivoting means further comprises the first spring having a longer length than the second spring.

5. The device of claim 2, wherein the piston comprises:
an open distal end dimensioned to receive the plunger; and
a pair of flanges extending outwardly from opposite sides of the open distal end of the piston, each of the flanges providing a distal seat for one of the springs.

6. The device of claim 3, wherein the piston comprises:
an open distal end dimensioned to receive the plunger; and
a pair of flanges extending outwardly from opposite sides of the open distal end of the piston, each of the flanges providing a distal seat for one of the springs.

7. The device of claim 4, wherein the piston comprises:
an open distal end dimensioned to receive the plunger; and
a pair of flanges extending outwardly from opposite sides of the open distal end of the piston, each of the flanges providing a distal seat for one of the springs.

8. The device of claim 5, further comprising:
a retention element extending into the housing from the distal end opening and dimensioned to be slidably received in the open distal end of the piston; and a hollow sleeve internally dimensioned to receive a syringe and having an open proximal end configured to engage the retention element through the distal end opening;

whereby, when a syringe is installed in the sleeve with the plunger extending from the distal end of the sleeve, the engagement of the sleeve with the retention element brings the plunger to bear against the proximal piston end so as to urge the piston toward its proximal position.

9. The device of claim 8, further comprising a locking mechanism, operable between the sleeve and the retention element, that substantially prevents relative movement between the sleeve and the retention element in response to the force applied by the piston to the plunger.

10. The device of claim 9, wherein the locking mechanism comprises:
internal threads in the retention element; and
external threads on the sleeve.

11. The device of claim 6, further comprising:
a retention element extending into the housing from the distal end opening and dimensioned to be slidably received in the open distal end of the piston; and a hollow sleeve internally dimensioned to receive a syringe and having an open proximal end configured to engage the retention element through the distal end opening;

whereby, when a syringe is installed in the sleeve with the plunger extending from the distal end of the sleeve, the engagement of the sleeve with the retention element brings the plunger to bear against the proximal piston end so as to urge the piston toward its proximal position.

12. The device of claim 11, further comprising a locking mechanism, operable between the sleeve and the retention element, that substantially prevents relative movement between the sleeve and the retention element in response to the force applied by the piston to the plunger.

13. The device of claim 12, wherein the locking mechanism comprises:
internal threads in the retention element; and
external threads on the sleeve.

14. The device of claim 7, further comprising:
a retention element extending into the housing from the distal end opening and dimensioned to be slidably received in the open distal end of the piston; and a hollow sleeve internally dimensioned to receive a syringe and having an open proximal end configured to engage the retention element through the distal end opening;

whereby, when a syringe is installed in the sleeve with the plunger extending from the distal end of the sleeve, the engagement of the sleeve with the retention element brings the plunger to bear against the proximal piston end so as to urge the piston toward its proximal position.

15. The device of claim 14, further comprising a locking mechanism, operable between the sleeve and the retention element, that substantially prevents relative movement between the sleeve and the retention element in response to the force applied by the piston to the plunger.

16. The device of claim 15, wherein the locking mechanism comprises:
internal threads in the retention element; and
external threads on the sleeve.

17. A device for actuating a syringe, wherein the syringe includes a barrel and a plunger movable axially within the barrel, the device comprising:
  a housing having a closed proximal end and a distal end with an opening therein dimensioned to receive the plunger;
  a retention element extending into the housing from the distal end opening;
  a piston disposed for longitudinal movement within the housing between a proximal position and a distal position, the piston having a proximal end and an open distal end dimensioned to slidingly receive the retention element when the piston is in its distal position;
  first and second springs disposed within the housing between the piston and the proximal end of the housing so as to bias the piston toward its distal position; and
  an externally-threaded sleeve internally dimensioned to receive a syringe and externally dimensioned to be received within the opening in the distal end of the housing and selectively threaded into and out of the retention element, the sleeve having an open proximal end through which the plunger of the syringe extends when a syringe is installed in the sleeve;
  whereby, when the sleeve is threaded into the retention element through the opening in the distal end of the housing with a syringe installed in the sleeve and the plunger of the syringe extending proximally through the open proximal end of the sleeve, the plunger of the syringe bears against the proximal end of the piston so as to urge the piston toward its proximal position.

18. The device of claim 17, further comprising:
  pivoting means, operative on the piston, for canting the piston with respect to the longitudinal axis of the housing when the piston is in its proximal position, and for causing the piston to pivot as it moves toward its distal position until the piston is oriented substantially coaxially with the longitudinal axis when the piston is at its distal position.

19. The device of claim 18, wherein the pivoting means comprises an internal width of the housing that narrows from the proximal end to the distal end.

20. The device of claim 19, wherein the pivoting means further comprises the first spring having a larger spring constant than the second spring.

21. The device of claim 19, wherein the pivoting means further comprises the first spring having a longer length than the second spring.

22. The device of claim 17, wherein the piston comprises:
  a pair of flanges extending outwardly from opposite sides of the open distal end of the piston, each of the flanges providing a distal seat for one of the springs.

23. The device of claim 18, wherein the piston comprises:
  a pair of flanges extending outwardly from opposite sides of the open distal end of the piston, each of the flanges providing a distal seat for one of the springs.

24. The device of claim 19, wherein the piston comprises:
  a pair of flanges extending outwardly from opposite sides of the open distal end of the piston, each of the flanges providing a distal seat for one of the springs.

25. The device of claim 20, wherein the piston comprises:
  a pair of flanges extending outwardly from opposite sides of the open distal end of the piston, each of the flanges providing a distal seat for one of the springs.

26. The device of claim 21, wherein the piston comprises:
  a pair of flanges extending outwardly from opposite sides of the open distal end of the piston, each of the flanges providing a distal seat for one of the springs.

27. An infusion system, comprising:
  a hollow sleeve having open proximal and distal ends;
  a housing having a proximal end and a distal end with an opening through which the proximal end of the hollow sleeve is received in the housing;
  a syringe having an outlet tip and a plunger, and installed in the sleeve with the outlet tip extending from the distal end of the sleeve and the plunger extending from the proximal end of the sleeve;
  a piston that bears against the plunger and that is disposed for longitudinal movement within the housing between a proximal position and a distal position;
  first and second springs disposed between the piston and the proximal end of the housing so as to bias the piston toward its distal position, thereby applying an axially-directed force component to the plunger; and
  means for maintaining the axially-directed force component substantially constant as the piston moves from its proximal position to its distal position.

28. The system of claim 27, wherein the means for maintaining comprises:
  pivoting means, operative on the piston, for canting the piston with respect to the longitudinal axis of the housing when the piston is in its proximal position, and for causing the piston to pivot as it moves toward its distal position until the piston is oriented substantially coaxially with the longitudinal axis when the piston is at its distal position.

29. The system of claim 28, wherein the pivoting means comprises an internal width of the housing that narrows from the proximal end to the distal end.

30. The system of claim 29, wherein the pivoting means further comprises the first spring having a larger spring constant than the second spring.

31. The system of claim 29, wherein the pivoting means further comprises the first spring having a longer length than the second spring.

32. The system of claim 27, wherein the piston comprises:
  an open distal end dimensioned to receive the plunger; and
  a pair of flanges extending outwardly from opposite sides of the open distal end of the piston, each of the flanges providing a distal seat for one of the springs.

33. The system of claim 28, wherein the piston comprises:
  an open distal end dimensioned to receive the plunger; and
  a pair of flanges extending outwardly from opposite sides of the open distal end of the piston, each of the flanges providing a distal seat for one of the springs.

34. The system of claim 29, wherein the piston comprises:
  an open distal end dimensioned to receive the plunger; and
  a pair of flanges extending outwardly from opposite sides of the open distal end of the piston, each of the flanges providing a distal seat for one of the springs.

35. The system of claim 30, wherein the piston comprises:
  an open distal end dimensioned to receive the plunger; and
  a pair of flanges extending outwardly from opposite sides of the open distal end of the piston, each of the flanges providing a distal seat for one of the springs.

36. The system of claim 31, wherein the piston comprises:
  an open distal end dimensioned to receive the plunger; and a pair of flanges extending outwardly from opposite sides of the open distal end of the piston, each of the flanges providing a distal seat for one of the springs.

37. The system of claim 32, further comprising:

a retention element extending into the housing from the distal end opening, externally dimensioned to be slidably received in the open distal end of the piston, and internally dimensioned to receive the sleeve.

38. The system of claim 37, further comprising a locking mechanism, operable between the sleeve and the retention element, that substantially prevents relative movement between the sleeve and the retention element in response to the axially-directed force component.

39. The system of claim 38, wherein the locking mechanism comprises:

internal threads in the retention element; and external threads on the sleeve.

40. The system of claim 33, further comprising:

a retention element extending into the housing from the distal end opening, externally dimensioned to be slidably received in the open distal end of the piston, and internally dimensioned to receive the sleeve.

41. The system of claim 40, further comprising a locking mechanism, operable between the sleeve and the retention element, that substantially prevents relative movement between the sleeve and the retention element in response to the force applied by the piston to the plunger.

42. The system of claim 41, wherein the locking mechanism comprises: internal threads in the retention element; and external threads on the sleeve.

43. The system of claim 34, further comprising:

a retention element extending into the housing from the distal end opening externally dimensioned to be slidably received in the open distal end of the piston, and internally dimensioned to receive the sleeve.

44. The system of claim 43, further comprising a locking mechanism, operable between the sleeve and the retention element, that substantially prevents relative movement between the sleeve and the retention element in response to the force applied by the piston to the plunger.

45. The system of claim 44, wherein the locking mechanism comprises:

internal threads in the retention element; and external threads on the sleeve.

46. The system of claim 35, further comprising:

a retention element externally dimensioned to be slidably received in the open distal end of the piston, and internally dimensioned to receive the sleeve.

47. The system of claim 46, further comprising a locking mechanism, operable between the sleeve and the retention element, that substantially prevents relative movement between the sleeve and the retention element in response to the force applied by the piston to the plunger.

48. The system of claim 47, wherein the locking mechanism comprises:

internal threads in the retention element; and external threads on the sleeve.

49. The system of claim 36, further comprising:

a retention element externally dimensioned to be slidably received in the open distal end of the piston, and internally dimensioned to receive the sleeve.

50. The system of claim 49, further comprising a locking mechanism, operable between the sleeve and the retention element, that substantially prevents relative movement between the sleeve and the retention element in response to the force applied by the piston to the plunger.

51. The system of claim 50, wherein the locking mechanism comprises:

internal threads in the retention element; and external threads on the sleeve.

* * * * *